(12) United States Patent
Bissonnette et al.

(10) Patent No.: US 6,571,600 B2
(45) Date of Patent: Jun. 3, 2003

(54) APPARATUS AND METHOD FOR MEASUREMENT OF COEFFICIENT OF RESTITUTION AND CONTACT TIME

(75) Inventors: Laurent C. Bissonnette, Portsmouth, RI (US); Charles A. Days, South Dartmouth, MA (US); Roman D. Halko, Chula Vista, CA (US); Emanuel Vieira, New Bedford, MA (US); Douglas C. Winfield, Seneca, SC (US)

(73) Assignee: Acushnet Company, Fairhaven, MA (US)

( * ) Notice: Subject to any disclaimer, the term of this patent is extended or adjusted under 35 U.S.C. 154(b) by 0 days.

(21) Appl. No.: 09/955,124

(22) Filed: Sep. 19, 2001

(65) Prior Publication Data

US 2003/0056567 A1 Mar. 27, 2003

(51) Int. Cl.⁷ .................................................. G01N 3/30
(52) U.S. Cl. ........................................ 73/12.02; 73/82
(58) Field of Search ............................ 73/12.04, 12.02, 73/12.01, 12.07, 12.08, 12.09, 78, 79, 82

(56) References Cited

U.S. PATENT DOCUMENTS

| | | | |
|---|---|---|---|
| 3,093,995 A | 6/1963 | Gordon | |
| 3,364,751 A | 1/1968 | Cornell et al. | |
| 3,509,736 A | 5/1970 | Saari | |
| 3,677,546 A | 7/1972 | Oetiker | 273/102.2 |
| 3,814,438 A | 6/1974 | Baron et al. | 273/176 |
| 3,999,756 A * | 12/1976 | Head | 463/64 |
| 4,071,242 A | 1/1978 | Supran | 273/61 |
| 4,289,023 A * | 9/1981 | Rader | 73/12.09 |
| 5,221,082 A | 6/1993 | Curchod | 273/185 |
| 5,245,862 A | 9/1993 | Zeiss | 73/79 |
| 5,419,565 A | 5/1995 | Gordon et al. | 273/374 |
| 5,437,457 A | 8/1995 | Curchod | 273/185 |
| 5,626,526 A | 5/1997 | Pao et al. | 473/156 |
| 5,672,809 A | 9/1997 | Brandt | 73/12.01 |
| 5,846,139 A | 12/1998 | Bair et al. | 473/156 |
| 5,863,255 A | 1/1999 | Mack | 473/152 |
| 6,385,559 B2 * | 5/2002 | Boehm | 473/223 |

* cited by examiner

*Primary Examiner*—Max Noori
(74) *Attorney, Agent, or Firm*—Swidler Berlin Shereff Friedman, LLP

(57) ABSTRACT

An apparatus and method for quantifying the stiffness of a golf ball or golf ball core under normal use conditions while also measuring the contact time, wherein an air cannon, or the like, is used to shoot an object horizontally against a block while the inbound and outbound velocities of the object are measured by two light gates separated by a given distance and the contact time is measured by optical sensors located at the block, and wherein the measured times and calculated velocities are then used to calculate the coefficient of restitution and contact time of the object.

36 Claims, 8 Drawing Sheets

APPARATUS AND METHOD FOR MEASUREMENT OF COEFFICIENT OF RESTITUTION AND CONTACT TIME

FIELD OF THE INVENTION

This invention relates generally to golf ball property measurement. Still more particularly, this invention relates to an apparatus and method for testing golf ball properties including coefficient of restitution and contact time.

BACKGROUND OF THE INVENTION

There is significant prior art for determining the hardness of a golf ball, including Atti compression, Reihle compression, the compression based on deformation of a ball under a 100 kg load and the compression of a ball under a 30 kg load. However, the prior art for identifying the stiffness of golf balls normally does not take into account the influence of deformation rate on "stiffness." That is, golf ball, or core, stiffness is typically measured by means of a low rate compression test. These tests are performed by applying a fixed load or a fixed deflection to the ball or core and by measuring displacement or load, respectively. The rate of load application in these tests range from 0.1 to 60 seconds, for the various industry standard tests (e.g., Atti, Reihle). The time for deformation of a golf ball on a typical driver during an ordinary impact is on the order of 0.0005 seconds, or, on the order of 2000 times faster than industry standard compression tests. It is well known that the polymeric materials used in golf balls have rate dependent stiffness. At high rates the stiffness may be as much as 10 times greater than stiffness measured at low rate. Therefore, prior art compression or stiffness measures usually do not reflect the stiffness of a ball in actual use conditions.

U.S. Pat. No. 3,509,736 to Saari discloses an apparatus for measuring the coefficient of restitution of spherical bodies. The apparatus applies a fixed velocity to the spherical body and computes the coefficient of restitution. The ball is held on a tee in an unrestrained manner. The ball is struck by a device causing the ball to move horizontally intercepting a beam from a photocell and continuing through a flight tube until it passes a light screen and a deflecting surface (such as a curtain). The device then uses the measurements to calculate the coefficient of restitution.

U.S. Pat. No. 5,245,862 to Zeiss discloses a portable testing device and method for determining the coefficient of restitution of a rebounding object. The method compares the bounce periods of successive bounces of the object. A ball is dropped on a reaction plate, the ball bounces at least three times on the reaction plate. Each impact is detected and the time of the bounce interval between successive bounces is measured. The coefficient of restitution is then calculated by comparing the bounce intervals as a ratio of the time between impacts of the second bounce interval to the first bounce interval. The device includes a reaction plate with a large mass in comparison with the ball, a transducer for registering the impact of the ball. A display is also included having a timer and a clock for measuring the bounce intervals and calculating the coefficient of restitution.

U.S. Pat. No. 5,672,809 to Brandt discloses a system for determining the coefficient of restitution between first and second pieces of sporting equipment. The system mounts a first piece of sporting equipment such as a bat, golf club or tennis racket. The first piece is held at a certain position and impacted by a second piece of sporting equipment, such as a baseball, golf ball or tennis ball. The device measures the velocity of the second piece of sporting equipment and the rebound velocity of the first piece of sporting equipment after impact. The coefficient of restitution is then determined using the measured information.

Nevertheless, it is desirable to have an apparatus to quantify the dynamic stiffness by means of contact duration while simultaneously acquiring coefficient of restitution.

SUMMARY OF THE INVENTION

The present invention is directed to an apparatus for measuring the physical properties of an object, the apparatus including: a propelling device that fires the object; a striking surface facing the propelling device; a sensing unit located between the striking surface and the propelling device, wherein the sensing unit has a measuring field covering a space between the propelling device and the striking surface, and wherein the sensing unit is capable of measuring the time it takes for the object to travel a distance in the measuring field of the sensing unit; and a computing unit that calculates the impact duration between the object and the striking surface and the Coefficient of Restitution of the object, wherein the computing unit is in communication with the sensing unit. In one embodiment, the propelling device is an air cannon. In another embodiment, the mass of the striking surface is at least about 50 times greater than the mass of the object. The object preferably includes a golf ball component.

In one embodiment, the sensing unit further includes a first sensing device at a first position and a second sensing device at a second position, the second sensing device being spaced apart from the first sensing device. Preferably, one of the sensing devices is a light gate. In one embodiment, the light gate is a solid state ballistics screen. In another embodiment, one of the sensing devices includes a plurality of sensors.

In one embodiment, the first sensing device has a sensing field covering a first predetermined plane and the second sensing device has a sensing field covering a second predetermined plane, the second predetermined plane being parallel and at a predetermined distance Y from the first predetermined plane. In one embodiment, the predetermined distance Y is about 12 inches or greater, and in another, the predetermined distance Y is about 4 feet or greater.

The apparatus can further include a third sensing device located near the striking surface for measuring the time in which the object is in contact with the striking surface. In one embodiment, the third sensing device includes a plurality of sensors. In another embodiment, the third sensing device has a sensing field covering a predetermined plane, wherein the the predetermined plane is preferably parallel and at a predetermined distance A from the striking surface. In a preferred embodiment, the predetermined distance A is about 1 inch or less, and more preferably about 0.25 inches or less.

In one embodiment, at least one of the sensors is a fiber optic sensor. Preferably, the fiber optic sensor includes a computer interface card and a fiber optic receiver electrically connected to the input of the computer interface card for counting the time in which the object is in contact with the striking surface.

The propelling device can fire the object in a horizontal or vertical direction.

The present invention is also directed to an apparatus for the simultaneous measurement of contact time and Coefficient of Restitution of an object, the apparatus including: a propelling device that fires the object; a striking surface facing the propelling device; at least one sensing device at a first position having a first sensing plane; a timing device triggered by the at least one sensing device; at least one camera triggered by the at least one sensing device to acquire at least a first and second pair of images before and after the object contacts the striking surface, respectively; and a computing unit that calculates the Coefficient of Restitution of the object and the contact time between the object and the striking surface. Each pair of images preferably includes a first and second image taken at two discrete time intervals.

In one embodiment, the apparatus further includes a second sensing device at a second position having a second sensing plane, wherein the second sensing device is parallel and at a predetermined distance A from the striking surface. The second sensing device preferably includes at least one fiber optic sensor. In one embodiment, the at least one fiber optic sensor includes a computer interface card and a fiber optic receiver electrically connected to the input of the computer interface card for counting the time in which the object stays past the second sensing device.

In another embodiment, the apparatus further includes a second camera to acquire at least a third and fourth pair of images before and after the object contacts the striking surface, respectively.

The present invention is also directed to a method of measuring Coefficient of Restitution and contact time of an object including the steps of: directing an object towards a striking surface; measuring a first velocity of the object before it contacts the striking surface; measuring impact duration of the object with the striking surface; measuring a second velocity of the object after it rebounds from the striking surface; and calculating the Coefficient of Restitution.

In one embodiment, the method further includes the step of providing at least one sensing unit having a measuring field covering at least a portion of space between an initial position of the object and the striking surface, wherein the at least one sensing unit measures the time required for the object to travel a distance in the measuring field of the sensing unit.

In another embodiment, the method further includes the step of providing a computing unit in communication with the at least one sensing unit that calculates the Coefficient of Restitution of the object and impact duration between the object and the striking surface.

The mass of the striking surface is preferably at least about 50 times greater than the mass of the object.

In one embodiment, the step of releasing the object is done horizontally, and in another embodiment, the step of releasing the object is done vertically.

In one embodiment, the method further includes the step of providing at least one camera to acquire at least a first and second pair of images before and after the object contacts the striking surface, respectively.

In another embodiment, the method further includes the step of providing a second sensing unit having a second measuring field covering a space between the at least one sensing unit and the striking surface, wherein the second sensing unit is parallel and at a predetermined distance from the striking surface.

In yet another embodiment, the method further includes the step of providing a second camera to acquire at least a third and fourth pair of images before and after the object contacts the striking surface, respectively.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the invention and in which.

DETAILED DESCRIPTION OF THE INVENTION

The present invention is directed to an apparatus for the simultaneous measurement of contact time and COR of a golf ball or golf ball core during normal use.

Figure 1:
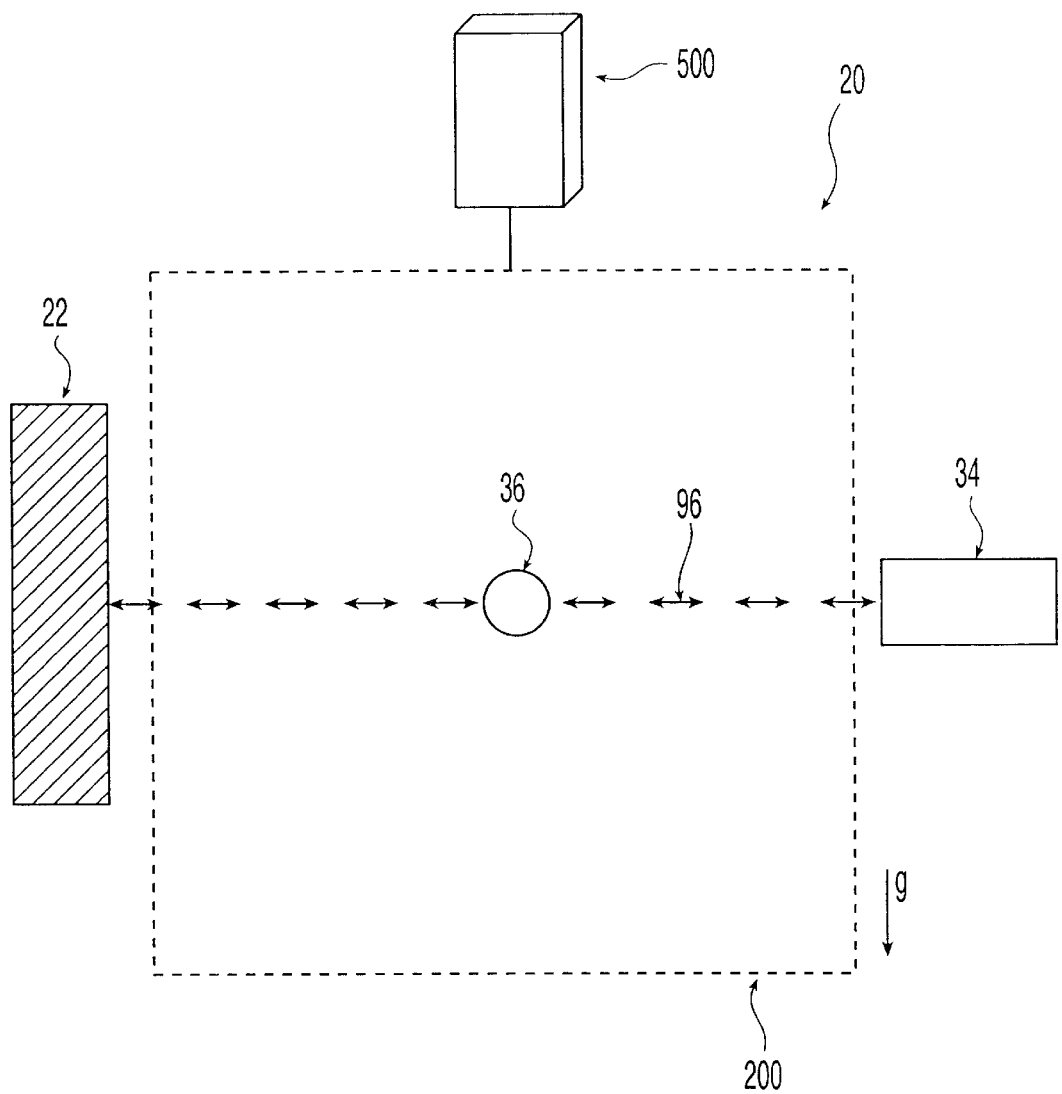
FIG. 1 is an arrangement of the apparatus of the present invention.

One embodiment of the invention, shown in FIG. 1, includes an apparatus 20 having an object 36, a propelling device 34, a striking surface 22, at least one sensing unit 200, and a computing unit 500 in communication with the sensing unit.

The object 36 can be any item that is able to be fired from the propelling device 34, for example, such as a golf ball or a golf ball core. The propelling device 34 can be any device that can propel the object toward the striking surface 22, for example, such as an air cannon, a linear motor, a translating belt, or the like. The propelling device 34 is preferably capable of propelling the object 36 at speeds from about 80 to about 180 feet/second (ft/s). In one embodiment, the propelling device 34 is an air cannon that propels the object 36 initially horizontally in the air toward the striking surface 22.

The line pressure (about 80 psi to about 90 psi) may enter a regulator in order to reduce the pressure in the air cannon to between about 40 psi to about 50 psi. In one embodiment, the air is stored in a tank (not shown). The tank can hold a volume of air, for example, about 80 cubic inches to about 90 cubic inches. A solenoid, e.g., such as a Mac Solenoid valve Model #56C-13-611JM, may be used to trigger a valve in order to release the stored pressurized air. An industrial valve, e.g., such as a Dubbin Industrial Valve C244 5001, may be used to release air into the main firing chamber to propel the object.

The firing pressure is controlled by a regulator, e.g., such as a Fairchild Regulator Model #10. The object velocity can be varied by varying the pressure with the regulator. As the object 36 is released from propelling device 34, it passes through at least one sensing device 30.

The sensing unit(s) 200 includes sensing devices which, in turn, include sensors capable of detecting passing objects. Suitable sensing devices may be obtained from Ordnance Industries, Model #6100 Solid State Ballistics Screens.

The computing unit 500 includes timers and a central processing unit (CPU), and is in communication with the sensing unit 200. The computing unit 500 can register the detection made by the sensing unit(s) 200 and can then calculate the physical response of the object 36 based on those detection measurements and other necessary information. Extra features, such as safety mechanisms and release plates, are preferably added to make the device easier and safer to use. A programmable logic controller (PLC), e.g., a Direct Logic 305 unit, may be used to automate operation.

In one embodiment, the striking surface 22 is a rigid planar surface. In another embodiment, the striking surface 22 is a block, e.g., a steel block, although a metal plate or a golf club head may be equally suitable. In one embodiment, the mass of the block is preferably at least about 50 times greater than the mass of the object 36. In another embodiment, the mass of the block is preferably at least about 100 times greater than the mass of the object 36.

As shown in FIG. 1, the propelling device 34 fires an object 36 at the striking surface 22 such that it passes through the sensing unit 200. Preferably, the object 36 strikes the striking surface 22 (e.g., in a direction relatively normal to the striking surface 22) and then bounces back (e.g., also in a direction relatively normal to the striking surface 22). The sensing unit(s) 200 detects the presence of the object 36, and in cooperation with timers, makes it possible to measure the time required for the object to travel between discrete distances within the space between the propelling device 34 and the striking surface 22. The computing unit 500 computes the COR and contact time of the object 36 using the measurements of time between activation of the sensing unit(s) 200 and discrete distances between sensing unit(s) 200.

The propelling device 34 can be situated in such a way that it fires the object in any direction. Preferably, the striking surface 22 is situated such that the striking surface 22 is perpendicular to the direction in which the propelling device 34 fires the object 36. In a preferred embodiment of the present invention, shown in FIG. 1, the propelling device 34 is situated in such a way that it fires the object 36 in a horizontal direction, i.e., perpendicular to the direction of gravity, denoted as g in FIG. 1, and the striking surface 22 is situated vertically, i.e., perpendicular to the direction in which the propelling device 34 fires the object 36. In another embodiment of the present invention, the propelling device 34 is situated in such a way that it fires the object 36 vertically in the upward direction and the striking surface 22 is situated horizontally, i.e., perpendicular to the direction in which the propelling device 34 fires the object 36.

Figure 2:
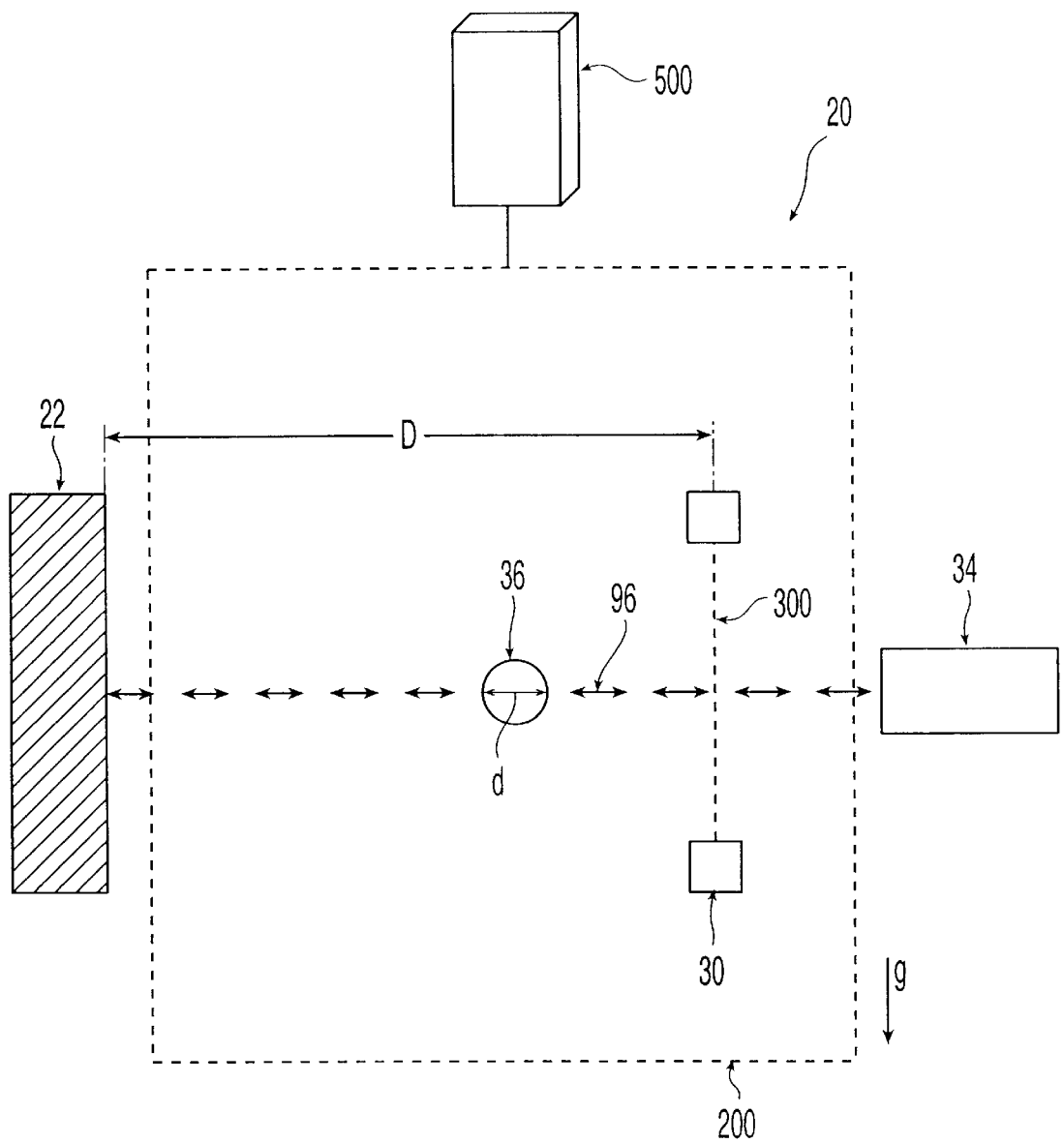
FIG. 2 illustrates one embodiment of the arrangement of the apparatus of FIG. 1 according to the present invention.

FIG. 2 shows another arrangement of the sensing unit 200 within the apparatus 20 shown in FIG. 1. The sensing unit 200 enables a time measurement for an object to travel between discrete points within the space between the propelling device 34 Ha and the striking surface 22. This measurement enables the calculation of the contact time between the object 36 and the striking surface 22. The sensing unit 200 also enables the calculation of the velocity of the object 36 before and after the object 36 contacts the striking surface 22. The calculation of the velocity, in turn, will enable the calculation of the COR of the object, because the COR of the object is the ratio of the outbound or rebound velocity to the inbound or impact velocity as the object strikes the striking surface in the normal direction.

In FIG. 2, the sensing unit 200 includes a sensing device 30, located in the space between the propelling device 34 and the striking surface 22. The sensing device 30 has a sensing field covering a sensing plane 300. The sensing device 30 preferably has an on/off switch such that, when any portion of the object 36 is in the sensing plane 300, the on/off status changes. The timer included in the computing unit 500, in communication with the sensing device 30, starts and stops in accordance with the changes in the on/off status of the sensing device 30. The time duration between the starts and stops is recorded by the central processing unit.

The sensing device 30 may be a sensor with an on/off status that can signal a timer when any portion of an object 36 is in the sensing plane 300, such as a light gate, a ballistics screen, an optical sensor, or the like. In one embodiment, the sensing device 30 is a light gate. In another embodiment, the sensing device 30 is a ballistics screen. In yet another embodiment, the sensing device 30 includes a coherent light source, such as a laser. The laser preferably has a wavelength from about 400 nanometers (nm) and about 800 nm. The laser beam is preferably split into multiple beams to form the sensing plane 300.

In one embodiment, the sensing device 30 includes a plurality of discrete sensors to provide for a widened sensing plane. The plurality of sensors may be arranged in any manner to allow sensing of an object passing through the predetermined plane. In one embodiment, a linear array of individual emitters may be arranged opposite a linear array of individual receivers. In another embodiment, a laser and beam splitter is used to emit light opposite a linear array of individual receivers. The emitters may be arranged across one edge of the predetermined plane of the sensing device and the receivers may be arranged across a directly opposing edge, although the arrangement of the plurality of sensors is not limited merely to these type of conformations. For example, an alternating linear array of individual emitters and receivers can be arranged opposite a similar alternating linear array of individual receivers and emitters. Alternately, either array may include staggering the emitters or receivers or both and/or arranging the emitters or receivers or both in blocks that may alternate, instead of alternating individual emitters and receivers.

Further, according to the invention, the plurality of sensors, or the planar emitters and receivers, may be arranged so that there are an even number of edges from which signals are being emitted and by which signals are being received. In the simplest case, with a planar emitter or a linear array of individual emitters on one edge and a planar receiver or a linear array of individual receivers on a directly opposing edge, the number would be two. In another embodiment, signals can be emitted and received as above, with other signals being emitted and received in the same manner, but oriented orthogonally in the plane to the previous signals. In this embodiment, the signals would crisscross and the number would be four (i.e., a square or rectangle where each side is capable of emitting or receiving a signal). In another embodiment, three such sets of signals can be emitted and received in the same manner as above, with each signal emitted or received being oriented at 60° to any other emitted or received signal; the number in this case would be six (i.e., a hexagon where each side is capable of emitting or receiving a signal). In yet another embodiment, four sets of signals can be emitted and received in the same manner as above, with each signal emitted or received being oriented at 45° to any other emitted or received signal; the number in this case would be eight (i.e., an octagon where each side is capable of emitting or receiving a signal). Alternately, the plurality of sensors may be arranged so that the individual emitters and receivers are situated opposite each other in any arrangement, so that the shape defined by those emitters and receivers is circular within the predetermined plane of the sensing device.

In FIG. 2, the sensing device 30 is arranged in such a way that the sensing plane 300 is parallel to the striking surface 22. The distance between the sensing plane 300 and the striking surface 22, D, is greater than the dimension of the object 36 (e.g., the diameter of the golf ball), d. After the object 36 is fired from the propelling device 34, it passes through the sensing plane 300. The sensing device 30 transmits a signal to the computing unit 500, causing the timer to start and the central processing unit to record the start time $t_1$, when the foremost point of the object 36 enters the sensing plane 300. The sensing device 30 then sends another signal to the computing unit 500 to register the time $t_2$, when the rearmost point of the object 36 leaves the sensing plane 300. When the object 36 rebounds back from the striking surface 22 and passes through the sensing plane 300, the sensing device 30 transmits another signal to the computing unit 500 to register the time $t_3$, when the foremost point of the object enters the sensing plane 300. The sensing device 30 sends yet another signal to the computing unit 500, registering time $t_4$, when the rearmost point of the object leaves the sensing plane 300.

Based on the assumption that the object 36 travels at a constant speed $v_1$, in a direction normal to the striking surface 22 before striking, and that the sensing plane 300 is parallel to the direction of gravity, the speed $v_1$ can be calculated as the ratio of the dimension of the object 36 to the time duration for the object 36 to go through the sensing plane 300 the first time: $v_1 = d/(t_2 - t_1)$.

Similarly, based on the assumption that the object 36 travels at another constant speed $v_2$, in a direction normal to the striking surface 22 after striking it, and that the sensing plane 300 is parallel to the direction of gravity, the speed $v_2$ can be calculated as the ratio of the dimension of the object 36 to the time duration for the object 36 to go through the sensing plane 300 the second time: $v_2 = d/(t_4 - t_3)$.

The Coefficient of the Restitution (COR) can therefore be calculated as $v_2/v_1$, or $(t_2-t_1)/(t_4-t_3)$.

Figure 3:
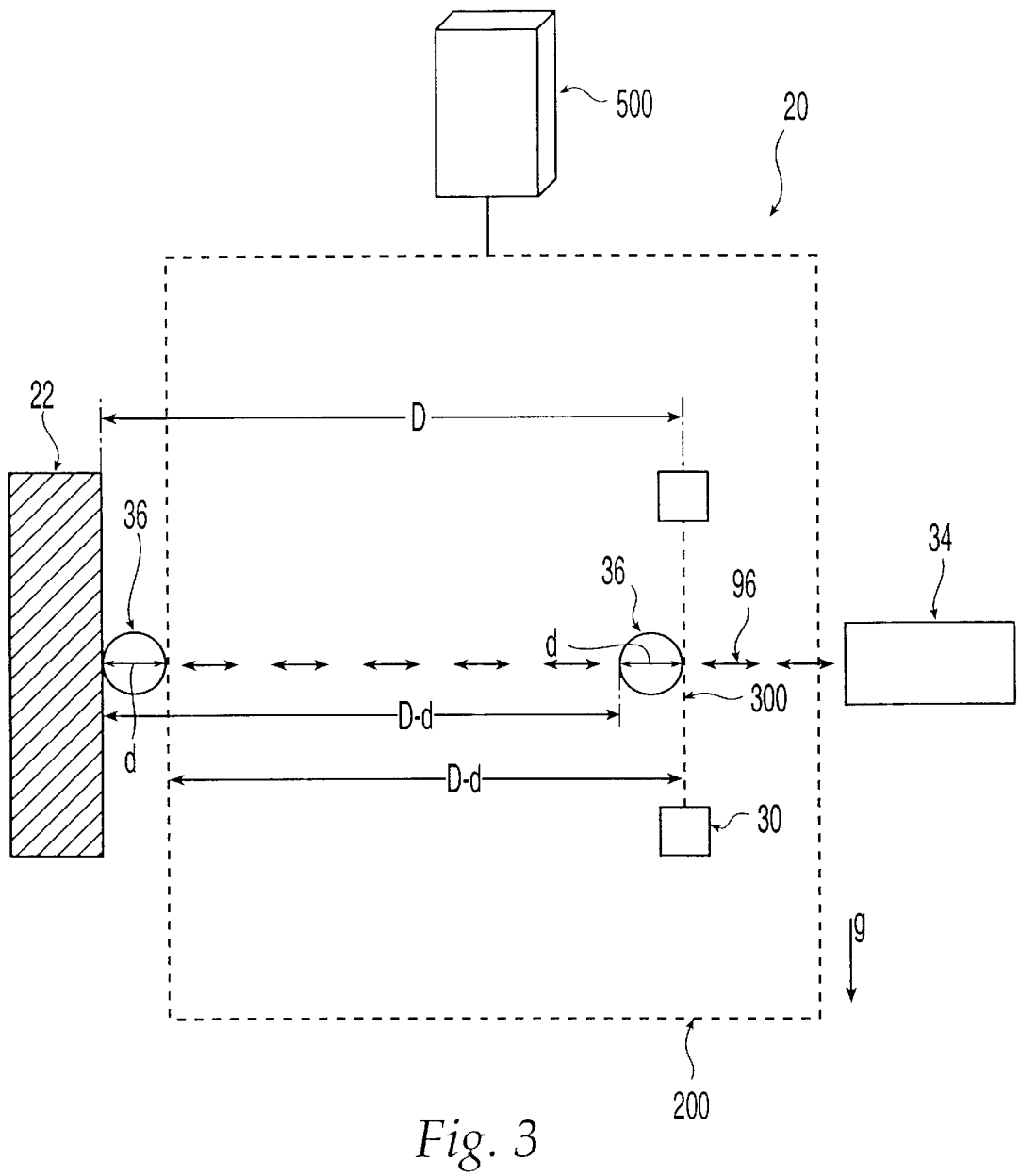
FIG. 3 illustrates an object in motion using the arrangement of the apparatus shown in FIG. 2 according to the present invention.

FIG. 3 illustrates that upon initially leaving the sensing plane 300, the object 36 travels a distance of (D−d) at the speed $v_1$ normal to the striking surface 22 before contact. This takes a time period of $P_1 = (D-d)/v_1$. Likewise, after leaving the striking surface 22, the object 36 travels a distance of (D−d) at the speed $v_2$ normal to the sensing plane 300 before entering the second time. This takes a time period of $P_2 = (D-d)/v_2$.

Because the object 36 stays past the sensing plane 300 (moving toward the striking surface 22) for a total time of $t_3-t_2$, i.e., after leaving the sensing plane 300 initially and before reentering the sensing plane 300 the second time, the contact time between the object 36 and the striking surface 22, $t_{bc}$, is:

$$t_{bc} = (t_3 - t_2) - P_1 - P_2$$

$$= (t_3 - t_2) - (D-d)/v_2 - (D-d)/v_2$$

$$= (t_3 - t_2) - (D-d)(t_4 - t_3)/d - (D-d)(t_2 - t_1)/d.$$

Figure 4:
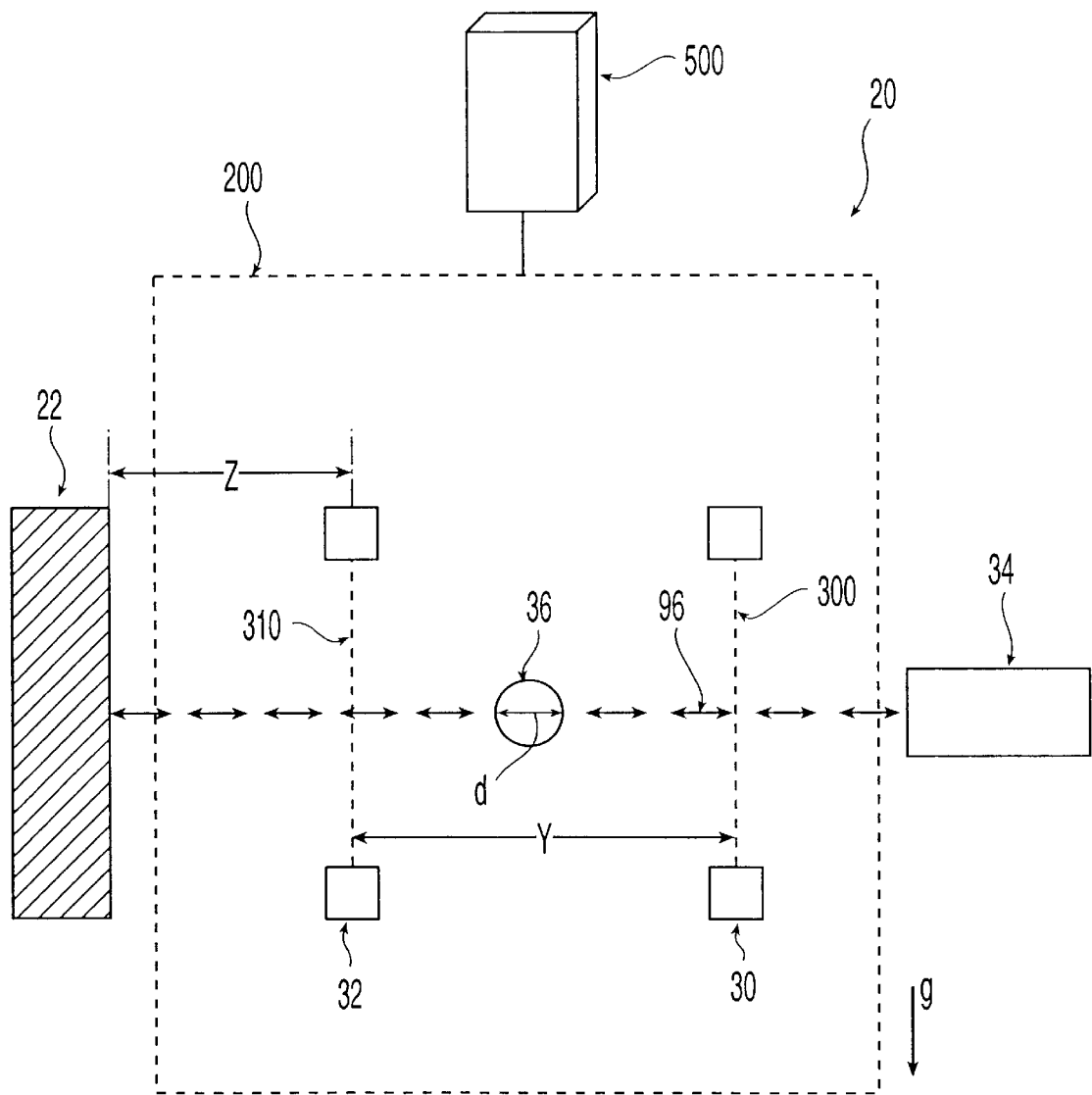
FIG. 4 illustrates one embodiment of the arrangement of the apparatus shown in FIG. 1. using two sensing devices according to the present invention.

FIG. 4 shows another arrangement of the apparatus 20 shown in FIG. 1. In comparison to the embodiment shown in FIGS. 2 and 3, in this embodiment, the sensing unit 200 includes a first sensing device 30 and a second sensing device 32, each having a sensing field covering a first sensing plane 300 and a second sensing plane 310, respectively. The second sensing device 32, located in the space between the first sensing device 300 and the striking surface 22 preferably has an on/off switch such that, when any portion of the object is in the second predetermined plane, the on/off status changes, as discussed with respect to the on/off switch of the sensing device 30 in FIGS. 2 and 3.

The second sensing device 32 may also be a sensor with an on/off status to signal a timer when any portion of an object 36 is in the second sensing plane 310, such as a light gate, a solid ballistics screen, or a fiber optic sensor. In a preferred embodiment, the second sensing device 32 is a light gate. In another preferred embodiment, the second sensing device 32 is a ballistics screen. In yet another preferred embodiment of the present invention, the second sensing device 32 includes a plurality of sensors to provide for a widened second sensing plane 310. In yet another embodiment, the second sensing device 310 includes a coherent light source, such as a laser. The laser preferably has a wavelength from about 400 nanometers (nm) and about 800 nm. The laser beam is preferably split into multiple beams to form the second sensing plane 310.

In FIG. 4, the second sensing device 32 is arranged in such a way that the second sensing plane 310, like the first sensing plane 300, is also parallel to the surface of the striking surface 22. The distance between the second sensing plane 310 and the first sensing plane 300 is Y and the distance between the second sensing plane 310 and the striking surface 22 is Z. Similar to FIGS. 2 and 3, Z is greater than d, the dimension of the object.

After the object 36 is fired from the propelling device 34, it passes through the first sensing plane 300 and then the second sensing plane 310. The first sensing device sends a signal to the computing unit 500, causing the timer in the computing unit to start and the central processing unit to record the time $t_1$, when the foremost point of the object 36 enters the first sensing plane 300. The second sensing device 32 also sends a signal to the computing unit 500, causing the timer in the computing unit to start at time $t_2$ and the central processing unit to record the time $t_2$, when the foremost point of the object 36 enters the second sensing plane 310. When the object 36 rebounds back from the striking surface 22 and passes through the second sensing plane 310 and then the first sensing plane 300, the second sensing device sends another signal to the computing unit 500 to register the time $t_3$, when the foremost point of the object 36 enters the second sensing plane 310 the second time. The first sensing device 30 also sends a signal to the computing unit 500 to register the time $t_4$, when the foremost point of the object 36 enters the first sensing plane 300 the second time.

Based on the assumption that the object 36 travels at a constant speed $v_1$, in a direction normal to the striking surface 22 before contact, and that the sensing planes 300, 310 are parallel to the direction of gravity, the speed $v_1$ can be calculated as the ratio of the predetermnined distance Y between the first sensing plane 300 and the second sensing plane 310 to the time duration for the object 36 to travel between the sensing planes:

$$v_1 = Y/(t_2 - t_1).$$

Similarly, based on the assumption that the object 36 travels at another Iconstant speed $v_2$, in a direction normal to the striking surface after contact, and that the sensing planes 300, 310 are parallel to the direction of gravity, the speed $v_2$ can be calculated as the ratio of the predetermined distance Y between the first and the second sensing planes 310 to the time duration for the object 36 to travel between the sensing planes:

$$v_2 = Y/(t_4 - t_3).$$

The Coefficient of the Restitution (COR) can therefore be calculated as $v_2/v_1$, or $(t_2-t_1)/(t_4-t_3)$.

Similar to the situation shown in FIG. 3, after entering the second sensing plane 310 the first time, the object 36 travels a distance of Z at the speed $v_1$, in a direction normal to the striking surface 22 before contact. This time period is $P_1 = Z/v_1$. Likewise, after leaving the striking surface 22, the object 36 travels a distance of (Z−d) at the speed $v_2$, normal to the second sensing plane 310, before entering it the second time. This time period is $P_2 = (Z-d)/v_2$.

Because the object 36 stays past (toward the striking surface with respect to) the second sensing plane 310 for a total time of $t_3 - t_2$, i.e., after leaving the second sensing plane 310 the first time and before entering the second sensing plane 310 the second time, the contact time between the object 36 and the striking surface 22, $t_{bc}$, is:

$$\begin{aligned} t_{bc} &= (t_3 - t_2) - P_1 - P_2 \\ &= (t_3 - t_2) - (Z-d)/v_2 - (Z-d)/v_1 \\ &= (t_3 - t_2) - (Z-d)(t_4 - t_3)/Y - Z(t_2 - t_1)/Y. \end{aligned}$$

Although FIG. 4 is a more complex arrangement and requires two sensing devices, instead of only one sensing device as shown in FIGS. 2 and 3, this arrangement has a distance Y between the two sensing planes, which is significantly larger than that dimension d of the object 36. This difference in dimensions provides enhanced accuracy for the velocity measurement of the object 36. In one embodiment, the distance Y is about 12 inches or greater. In another embodiment, the predetermined distance Y is about 4 feet or greater.

Figure 5:
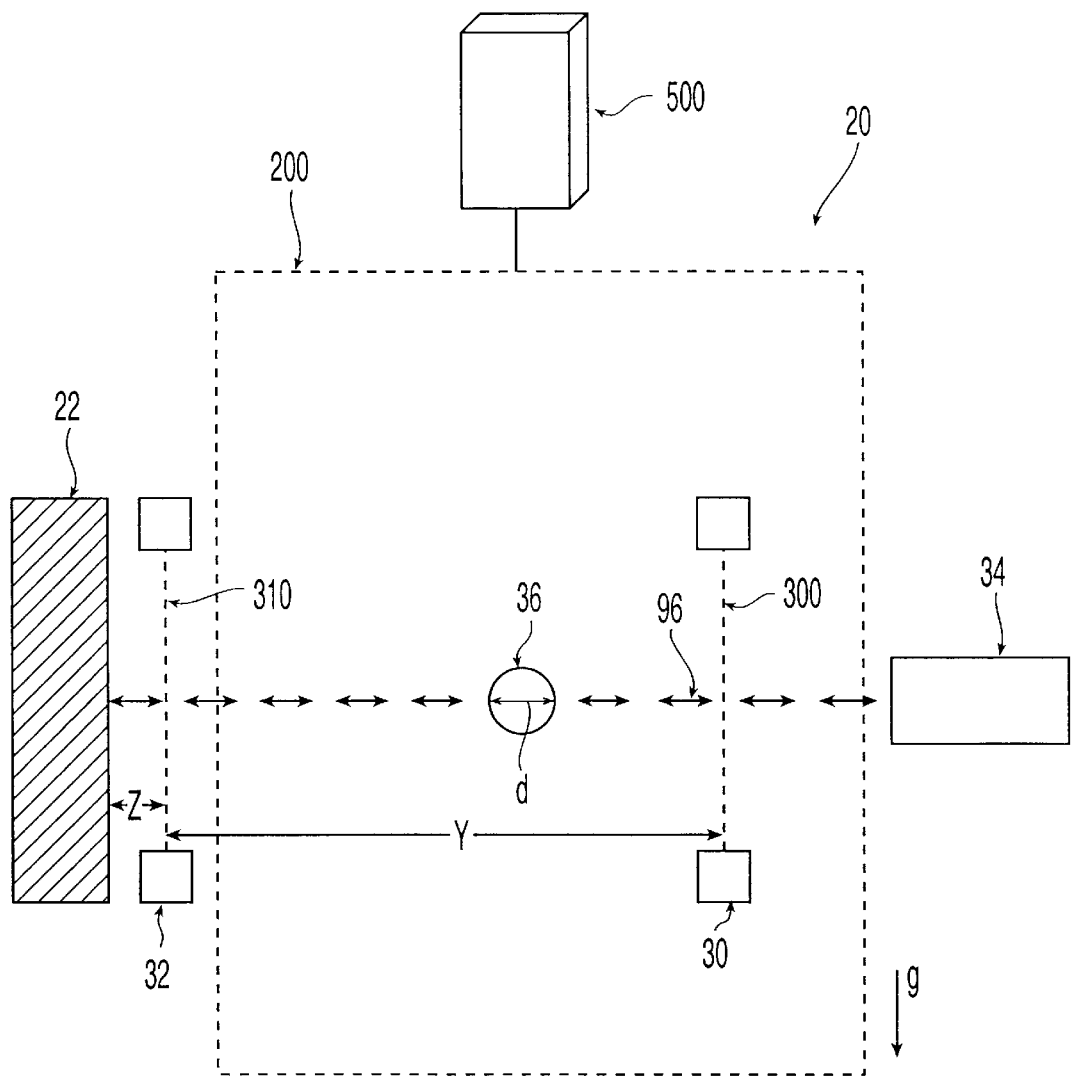
FIG. 5 illustrates another embodiment of the arrangement of the apparatus shown in FIG. 1 using two sensing devices according to the present invention.

FIG. 5 shows another arrangement of the apparatus 20 using two sensing devices. In this arrangement, the second sensing device 32 is located much closer to the striking surface 22 than as illustrated in FIG. 4. Consequently, the distance between the second sensing plane 310 and the striking surface, Z, is less than the dimension, d, of the object 36. In this embodiment, the first and second sensing devices 30, 32 send signals to the computing unit 500 in the same way prior to the object contacting the striking surface 22, i.e., after the object 36 is fired from the propelling device 34, it passes through the first sensing plane 300 and then the second sensing plane 310. The first sensing device 30 sends a signal to the computing unit 500 to register the time $t_1$, when the foremost point of the object enters the first sensing plane 300. The second sensing device 32 also sends a signal to the computing unit 500 to register the time $t_2$, when the foremost point of the object 36 enters the second sensing plane 310.

However, the first and second sensing devices 30, 32 send signals to the computing unit 500 in a different way after the object contacts the striking surface 22. Because the distance between the second sensing plane 310 and the striking surface 22, Z, is less than d, the dimension of the object, the object can not leave the second sensing plane 310 before contacting the striking surface 22. The object is also not able to enter the second sensing plane 310 a second time after contacting the striking surface 22. Instead, the object remains in the second sensing plane 310 when in contact with the striking surface 22. Thus, when the object 36 rebounds back from the striking surface 22, the second sensing device 32 sends a signal to the computing unit 500 to register the time $t_3$, when the rearmost point of the object 36 leaves the second sensing plane 310, instead of when the foremost point of the object enters the second sensing plane 310 the second time. The first sensing device 30, like before, sends a signal to the computing unit 500 to register the time $t_4$, when the foremost point of the object enters the first sensing plane 300 the second time.

Based on the assumption that the object travels at a constant speed $v_1$, in a direction normal to the striking surface before contact, and that the sensing planes 300, 310 are parallel to the direction of gravity, the speed $v_1$ can be calculated as the ratio of the distance Y between the sensing planes 300, 310 to the time duration for the object to travel between the first and second sensing planes 300, 310 the first time:

$$v_1 = Y/(t_2 - t_1).$$

Similarly, based on the assumption that the object travels at another constant speed $v_2$, in a direction normal to the striking surface after contact, and that the sensing planes 300, 310 are parallel to the direction of gravity, the speed $v_2$ can be calculated as the ratio of the distance Y between the first and the second predetermined planes minus the object diameter d to the time duration for the object to travel between the sensing planes 300, 310 the second time:

$$v_2 = (Y-d)/(t_4 - t_3).$$

The Coefficient of the Restitution (COR) can therefore be calculated as $v_2/v_1$, or $(Y-d)(t_2-t_1)/[Y(t_4-t_3)]$.

After entering the second sensing plane 310, the object 36 travels a distance of D at the speed $v_1$ normal to the striking surface 22 before contact. This requires a time period of $P_1 = D/v_1$. Likewise, after leaving the striking surface, the object travels a distance of D at the speed $v_2$ normal to the second sensing plane 310 before leaving the second sensing plane 310. This requires a time period of $P_2 = D/v_2$.

Because the object 36 stays within the second sensing plane 310 for a total time of $t_3 - t_2$ after entering and before leaving the second sensing plane 310, the contact time the object 36 makes with the striking surface 22, $t_{bc}$, is:

$$\begin{aligned} t_{bc} &= (t_3 - t_2) - P_1 - P_2 \\ &= (t_3 - t_2) - Z/v_2 - Z/v_1 \\ &= (t_3 - t_2) - Z(t_4 - t_3)/(Y-d) - Z(t_2 - t_1)/Y. \end{aligned}$$

As discussed with respect to the embodiment shown in FIG. 4, although FIG. 5 shows a more complex dual sensing device arrangement, the distance Y between the two sensing planes 300, 310, which is significantly larger than the dimension of the object d, provides a more accurate measurement of the velocity of the object 36 and contact time with the striking surface 22.

In order for this embodiment to provide accurate measurements, the distance Z between the second sensing plane 310 and the striking surface 22 must be small. In a preferred embodiment of the present invention, the distance Z is about 1 inch or less. In another preferred embodiment of the present invention, the distance Z is about 0.25 inches or less. In yet another preferred embodiment of the present invention, the distance Z is about 0.13 inches or less.

Figure 6:
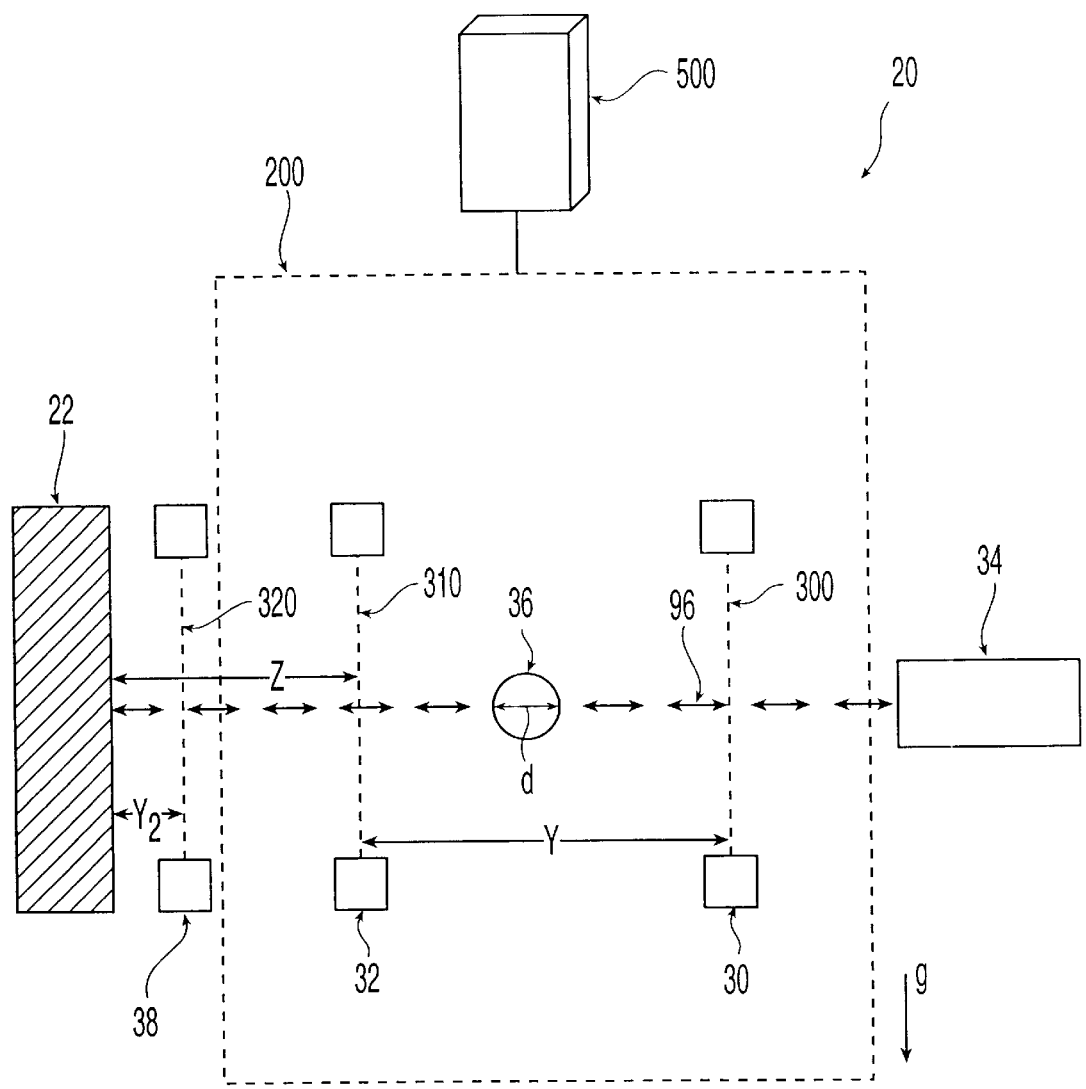
FIG. 6 illustrates another embodiment of the arrangement of the apparatus shown in FIG. 1. using three sensing devices according to the present invention.

FIG. 6 shows another arrangement of apparatus 20 of the present invention. In this embodiment, the sensing unit further includes a third sensing device 38, in addition to the first sensing device 30 and second sensing device 32 of FIGS. 4 and 5. The third sensing device 38 is located near the striking surface 22. It has a sensing area covering an third sensing plane 320 that is parallel to the striking surface 22. The third sensing device 38 is designed specifically for the purpose of enabling the registration of the time duration during which any part of the object 36 is in the third sensing plane 320. According to this embodiment, after the object 36 is fired from the propelling device 34, the first and second sensing devices 30, 32 signal the computing unit 500 to register the time duration $t_1$ between the time when the foremost point of the object 36 enters the first sensing plane 300 and the time when the foremost point of the object 36 enters the second sensing plane 310. The computing unit 500 also registers the time duration $T_b$ during which the object 36 stays in the third sensing plane 320. When the object 36 rebounds back from the striking surface 22, the sensing devices signal the computing unit 500 to register the time duration $t_2$ between the time when the foremost point of the object 36 enters the second sensing plane 310 the second time and the time when the foremost point of the object enters the first sensing plane 300 the second time.

Based on the assumption that the object 36 travels at a constant speed $v_1$, in a direction normal to the striking surface 22 before contact, and that the sensing planes are parallel to the direction of gravity, the speed $v_1$ can be calculated as the ratio of the predetermined distance Y between the first and the second sensing planes 300, 310 to the time duration for the object to travel between the two sensing planes the first time:

$$v_1 = Y/t_1.$$

Similarly, based on the assumption that the object travels at another constant speed $v_2$, in a direction normal to the striking surface 22 after contact, the speed $v_2$ can be calculated as the ratio of the predetermined distance Y between the first and the second sensing planes 300, 310 to the time duration for the object to travel between the two sensing planes the second time:

$$v_2 = Y/t_2.$$

The Coefficient of the Restitution (COR) can therefore be calculated as $v_2/v_1$, or $t_1/t_2$, and the contact time between the object 36 and the striking surface 22, $t_{bc}$, can be considered equivalent to the time duration $T_b$ during which the object 36 stays in the second sensing plane 310 minus the inbound and outbound flight time to transit the distance Y2. Thus, $t_{bc} = T_b - Y_2/v_1 - Y_2/v_2$.

In order for this embodiment to provide accurate measurements, the distance $Y_2$ between the third sensing plane 320 and the striking surface 22 must be small. In a preferred embodiment of the present invention, the distance $Y_2$ is about 1 inch or less. In another preferred embodiment of the present invention, the distance $Y_2$ is about 0.25 inches or less. In yet another preferred embodiment of the present invention, the distance $Y_2$ is about 0.13 inches or less.

The striking surface 22 in this embodiment is preferably a rigid block or metal plate. The apparatus 20 is preferably set up to operate in a horizontal position with the sensing planes 300, 310, 320 parallel to the direction of gravity.

In one embodiment, the third sensing device 38 is a fiber optic sensor including a planar optical emitter and a planar optical receiver adjacent to the striking surface 22. The use of fiber optic sensors is advantageous because: (1) balls and cores are usable without modification of the apparatus; (2) fiber optic components and associated electronic signal processing hardware may be designed to operate at switching frequencies of 500 kHz which resolves contact time to an accuracy of 2 microseconds; and (3) the use of fiber optics significantly reduces problems associated with radio frequency induced electronic noise.

Contact time may also be measured by placing conductive foil on the object 36 and by placing a lattice of conductors on the striking surface 22. When the object 36 is in contact with the striking surface 22, the resistance of the lattice can vary measurably. Contact duration is generally linked to the duration of the resistance change. This technique is effective but can have deficiencies in comparison to the optical technique. The deficiencies can include: 1) alteration of the balls or cores to have conductive surfaces; 2) the conductive lattice sustaining damage after repeated impact; and 3) the electronic circuits required to measure resistance variations are prone to radio frequency noise and do not operate at as high a frequency as the optical technique disclosed above.

Figure 7:
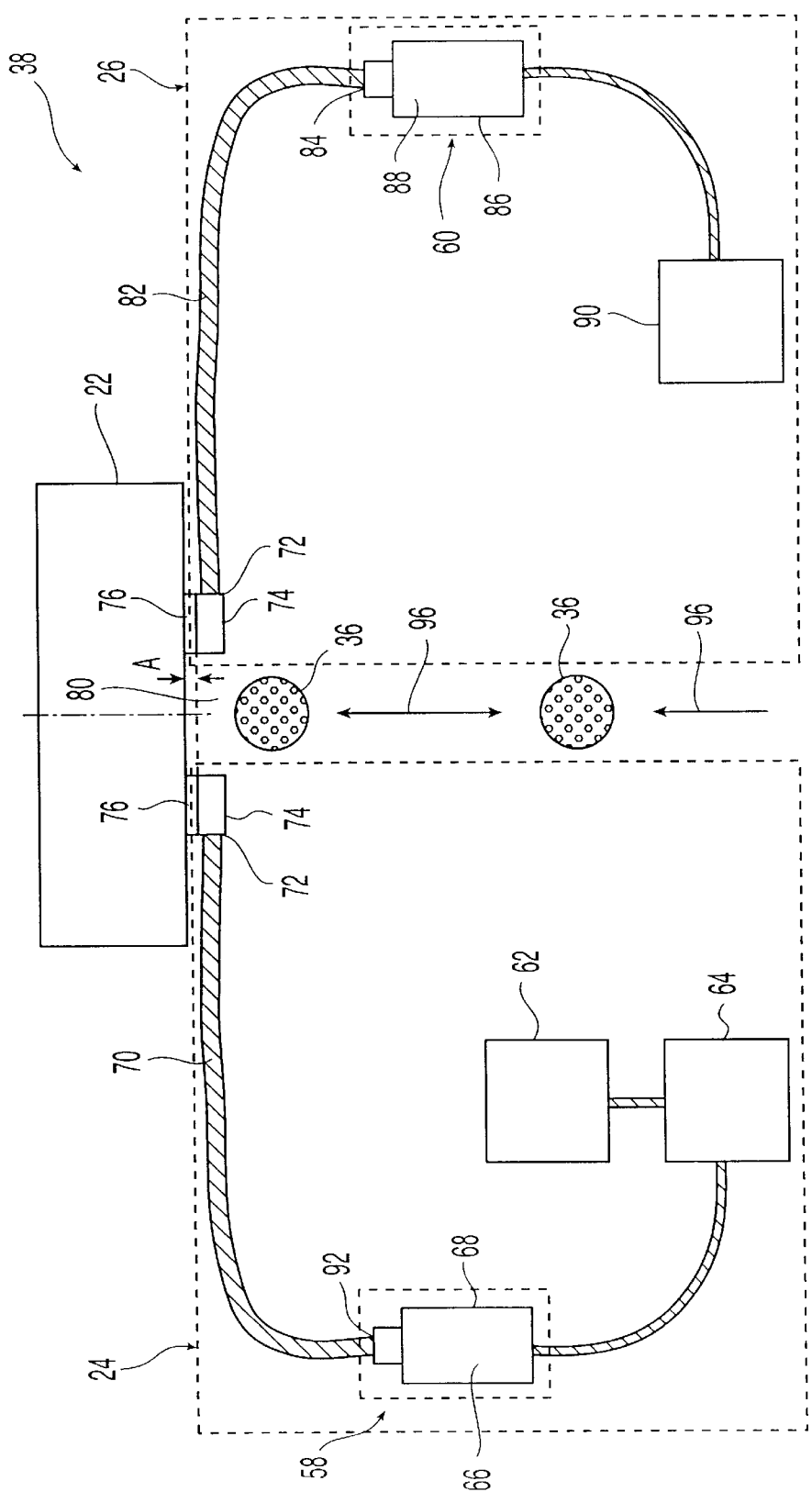
FIG. 7 is a schematic of the third optical sensor in accordance with a preferred embodiment of FIG. 6 according to the present invention.

FIG. 7 shows a preferred third sensing device 38 in detail. The third sensing device 38 includes a light or other energy source 58 and receiver 60. The planar emitter 24, or other energy transmitter, preferably includes a number of components. A power supply 62, e.g., such as a regulated 12 volt 0.5 amp DC power supply, is connected to an adjustable monolithic regulator 64. This adjustable voltage is applied to an energy emitter 66, such as a lamp, e.g., a #349 miniature incandescent lamp, that is preferably within an enclosed housing 68. The housing 68 should generally accept a standard fiber optic assembly 70, e.g., such as one that has a thin, flat dispersion at the opposed end 72. The opposed end may be held in position, e.g., by a Ultra High Molecular Weight polyethylene panel (UHMW panel) 74, held and constrained in position by flat ceramic magnets 76. Typically, the panel 74 is slightly removed from the striking surface 22 by a short distance A, which is preferably about 0.25 inches or less, and is cut away to form an opening 80 in the center such that a golf ball may pass through and strike the rigid block 78. A fiber assembly 70 is placed at this opening 80 and opposes a second fiber assembly 82 directly across the opening 80, which forms part of the optical planar receiver 26. At the opposite end 84, 92 of each fiber assembly 82, 70 is an identical fiber assembly contained within an enclosed housing 68, 86 is an optic receiver 66, 88.

In a preferred embodiment, each optic receiver 66, 88 is an inverting fiber optic receiver, e.g., such as Honeywell Model HFD-3031. Each inverting fiber optic receiver is electrically connected to the input of a counter/timer computer interface card 64, 90. The counter/timer computer interface card 64, 90 preferably has an operating frequency of about 500 kHz or greater, more preferably about 1 MHz or greater. The operating frequency should be advantageously selected to provide as much accuracy and resolution as possible for contact time and COR measurements.

Figure 8:
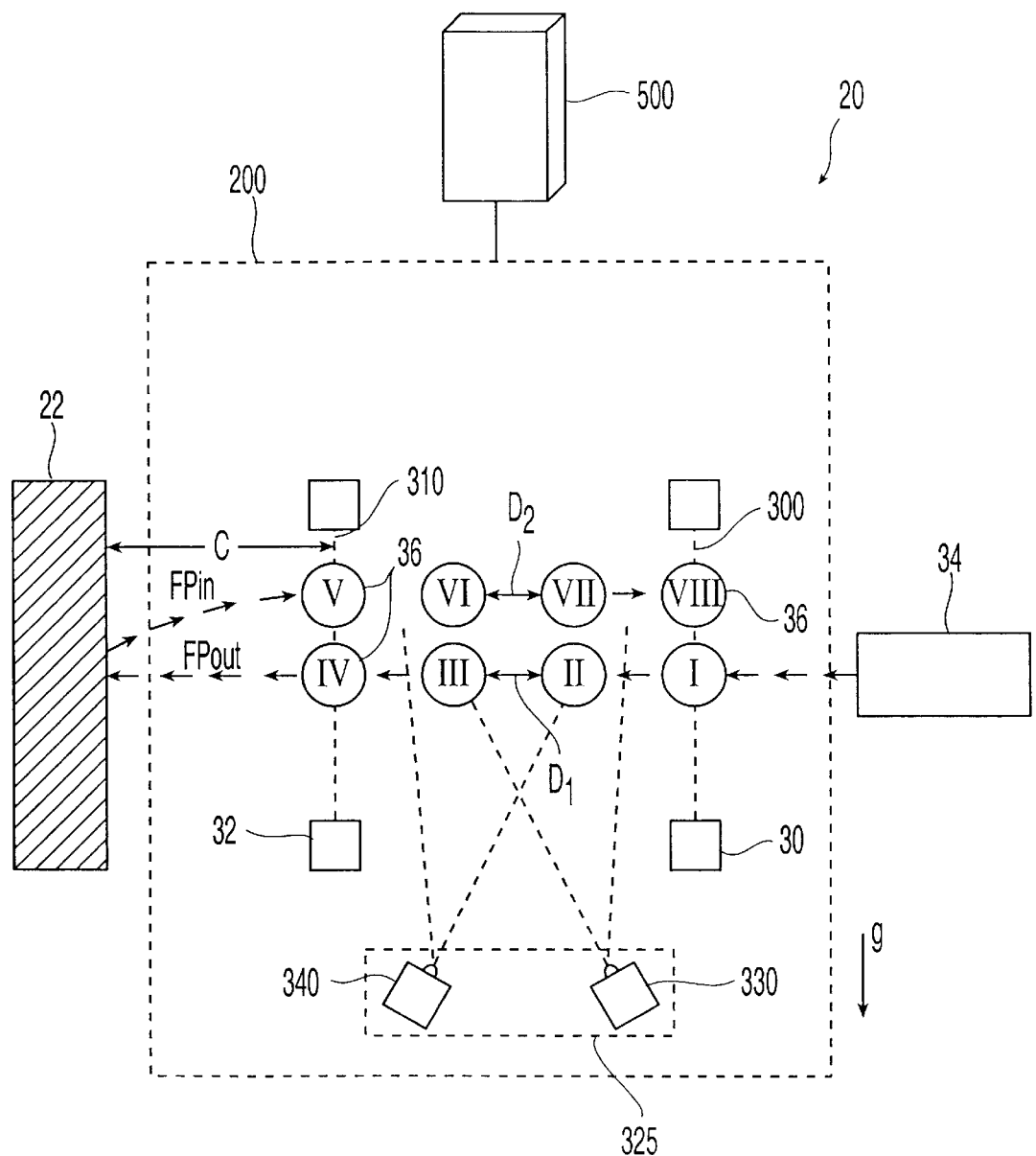
FIG. 8 illustrates another embodiment of the arrangement of the apparatus shown in FIG. 1, using optical cameras according to the present invention.

Another embodiment of the present invention is shown in FIG. 8, similar to the arrangement shown in FIG. 4 using two sensing devices in combination with one or more optical cameras. In this embodiment, the sensing unit 200 includes a first sensing device 30 and a second sensing device 32, each having a sensing field covering a first is sensing plane 300 and a second sensing plane 310, respectively, that are parallel to the surface of the striking surface 22. A camera system 325 includes at least one camera and lighting unit. At least two optical cameras are preferred to triangulate the space with triggers and timers. FIG. 8 illustrates this embodiment in which the camera system 325 includes a first camera 330 and a second camera 340, positioned in between the sensing planes 300, 310.

The sensing devices 30, 32 may also be sensors with an on/off status to simultaneously signal at least one timer in the computing unit 500 and the camera system 325 when any portion of an object 36 passes through the first or second sensing planes 300, 310. For example, the sensing devices 30, 32 may be coherent light sources, such as lasers. The sensing devices 30, 32 may communicate via an asynchronous protocol through the computing device 500 to the camera system 325 and timers to control activation.

The camera system 325 preferably includes a lighting system, such as a dual strobe lighting unit, and a filtering system, for each camera used. The cameras 330, 340 used in this embodiment are preferably electro-optical cameras with light-receiving apertures, shutters, and light sensitive silicon panels as discussed in U.S. Pat. No. 5,575,719, which is incorporated in its entirety by reference herein. Multishutter cameras may also be used as disclosed in co-pending application Ser. No. 09/379,592, the contents of which are incorporated in its entirety by reference herein. Suitable commercially available cameras include, but are not limited to, ELECTRIM EDC-1000U Computer Cameras (EDC Cameras) from Electrim Corporation in Princeton, N.J. Charge coupled device or CCD cameras are preferred, but TV-type video cameras are also useful.

In one embodiment, the camera is a CCD camera with about 90,000 pixels or greater. In a preferred embodiment, the camera has about 300,000 pixels or greater, and, more preferably, the camera has about 1,000,000 pixels.

FIG. 8 illustrates an object 36 in various positions I–IV after firing from the propelling device 34 on the outbound trip to the striking surface 22, and on the return (inbound) flight, V–VIII, after contacting the striking surface 22. After the object 36 is fired from the propelling device 34, it passes through the first sensing plane 300. When the foremost point of the object 36 enters the first sensing plane 300 (Position I), the first sensing device 30 sends a signal to the computing unit 500 to activate the camera system 325. Once activated, the cameras 330, 340 each acquire a first image, e.g., Position II. After a known time interval ($t_c$), the cameras 330, 340 each acquire a second image, e.g., Position III.

The object 36 then moves through the second sensing plane 310 (Position IV) and the computing unit 500 receives a signal from the sensing device 32 to store a time $t_2$. The object 36 then continues along the flight path ($FP_{out}$), impacts the striking surface 22, and rebounds, following the inbound flight path ($FP_{in}$). As the object 36 moves into Position V, the sensing device 32 again activates the cameras 340, 330 and sends a signal to the computing unit to record a time $t_3$. The cameras 340, 330 each acquire a pair of images, e.g., Positions VI and VII.

The first and second images acquired by each camera make it possible to triangulate the spacial coordinates of the object 36 at each image capture, which allows for the determination of the distance between the object 36 at Positions II and III, and Positions VI and VII, to be determined. In another embodiment, however, a dual camera system is used, but each camera has a single flash. In yet another embodiment, a single camera is used. Because a dual camera system is used.

Based on the assumption that the object 36 travels at a constant speed $v_1$, in a direction normal to the striking surface 22 before contact, and that the sensing planes 300, 310 are parallel to the direction of gravity, the speed $v_1$ can be calculated as the ratio of the distance $D_1$ between the first and second image and the time between each image capture $t_c$:

$$v_1 = D_1/t_c.$$

Similarly, based on the assumption that the object 36 travels at another constant speed $v_2$ on the inbound flight path ($FP_{in}$) after contact, in a direction normal to the striking surface, and that the sensing planes 300, 310 are perpendicular to the direction of gravity, the velocity $v_2$ can be calculated as the ratio of the distance $D_2$ between the first and second images and the time between each image capture $t_c$:

$$v_2 = D_2/t_c.$$

The Coefficient of the Restitution (COR) can therefore be calculated as $v_2/v_1$, or $D_2/D_1$.

Similar to the situation shown in FIG. 4, after passing through the sensing unit 32 (Position IV), wherein time $t_2$ is logged, the object travels a distance of C at the speed $v_1$, in a direction normal to the striking surface 22 before contact. This time period is $P_1 = C/v_1$. Likewise, after leaving the striking surface 22, the object 36 travels a distance of C at the speed $v_2$, in a direction normal to the second sensing plane 310, before passing back through the sensing unit 32 at time $t_3$ (Position V). This time period is $P_2 = C/v_2$.

Because the object 36 stays past (toward the striking surface with respect to) the sensing unit 32 for a total time of $t_3 - t_2$, the contact time between the object 36 and the striking surface 22, $t_{bc}$, is:

$$\begin{aligned} t_{bc} &= (t_3 - t_2) - P_1 - P_2 \\ &= (t_3 - t_2) - C/v_1 - C/v_2 \\ &= (t_3 - t_2) - C(t_c)/D_1 - C(t_c)/D_2. \end{aligned}$$

Any number of ways can be used to calibrate the apparatus 20. For example, when calibrating the system using sensing devices, but no optical cameras, an object 36 may be attached to a measurement device, e.g., such as a dial indicator (not shown). The object is introduced into the path 96 of the normal flight of the object 36 toward the striking surface 22, as shown in FIG. 7. When sufficient light is obstructed, the optic receiver will indicate a HIGH reading. The distance between the striking surface 22 and the position of the object 36 when the receiver indicates a HIGH signal is measured. In the embodiment shown in FIG. 6, this distance is $Y_2$ and is required in the computation of the contact time. The time it takes for the object 36 to contact the striking surface 22 and rebound through the distance $Y_2$ can be subtracted from the duration of time that the HIGH signal is maintained to correct the contact time measurement.

EXAMPLES

These and other aspects of the present invention may be more fully understood by reference to the following tests. While these tests are meant to be illustrative of the apparatus made according to the present invention, the present invention is not meant to be limited by the following tests.

Testing was performed on various balls using the apparatus of the present invention. As is shown in Table 1 below, the HP Eclipse™, a double core ball, and the DT™ two-piece, a two-piece ball, have similar compressions when measured on an Atti compression machine, yet their contact times or impact stiffness measured at a velocity of about 250 ft/s are significantly different. The HP Eclipse™ has a much longer contact time or lower impact stiffness, and a softer feel.

TABLE 1

| Ball | Atti Compression | Velocity | COR | Contact Time |
|---|---|---|---|---|
| DT 2-Piece ™ | 92.7 | 254.43 | 0.817 | 422.9 |
| HP Eclipse ™ | 92.2 | 250.67 | 0.793 | 451.4 |

Thus, contact time is a better measure of ball stiffness than static compression testing.

While it is apparent that the illustrative embodiments of the invention herein disclosed fulfills the objectives stated above, it will be appreciated that numerous modifications and other embodiments may be devised by those skilled in the art. For example, another device could be used for shooting the object out toward the massive block, the device may be oriented at any angle with respect to gravity, or other calculations based on simple trigonometric functions may be employed along with the recorded measurements to account for the effect of the gravitational force on the calculation of the COR. Therefore, it will be understood that the appended claims are intended to cover all such modifications and embodiments which come within the spirit and scope of the present invention.

What is claimed is:

1. An apparatus for measuring the physical properties of a golf ball, the apparatus comprising:
   a striking surface;
   a propelling device facing the striking surface that fires the golf ball toward the striking surface;
   a sensing unit located between the striking surface and the propelling device, wherein the sensing unit has a measuring field covering a space between the propelling device and the striking surface, and wherein the sensing unit is capable of measuring the time it takes for the golf ball to travel a distance in the measuring field of the sensing unit; and
   a computing unit that calculates the impact duration between the golf ball and the striking surface and the Coefficient of Restitution of the golf ball, wherein the computing unit is in communication with the sensing unit.

2. The apparatus of claim 1, wherein the propelling device is an air cannon.

3. The apparatus of claim 1, wherein the mass of the striking surface is at least about 50 times greater than the mass of the object.

4. The apparatus of claim 1, wherein the propelling device fires the object vertically.

5. The apparatus of claim 1, wherein the sensing unit further comprises:
   a first sensing device at a first position; and
   a second sensing device at a second position, the second sensing device being spaced apart from the first sensing device.

6. The apparatus of claim 5, wherein one of the sensing devices is a light gate.

7. The apparatus of claim 6, wherein the light gate is a solid state ballistics screen.

8. The apparatus of claim 5, wherein one of the sensing devices comprises a plurality of sensors.

9. The apparatus of claim 5, wherein the first sensing device has a sensing field covering a first predetermined plane.

10. The apparatus of claim 9, wherein the second sensing device has a sensing field covering a second predetermined plane, said second predetermined plane being parallel and at a predetermined distance Y from said first predetermined plane.

11. The apparatus of claim 10, wherein the predetermined distance Y is about 12 inches or greater.

12. The apparatus of claim 11, wherein the predetermined distance Y is about 4 feet or greater.

13. The apparatus of claim 5, further comprising a third sensing device located near the striking surface for measuring the time in which the object is in contact with the striking surface.

14. The apparatus of claim 13, wherein the third sensing device comprises a plurality of sensors.

15. The apparatus of claim 13, wherein the third sensing device has a sensing field covering a predetermined plane.

16. The apparatus of claim 15, wherein the predetermined plane is parallel and at a predetermined distance A from the striking surface.

17. The apparatus of claim 16, wherein the predetermined distance A is about 1 inch or less.

18. The apparatus of claim 17, wherein the predetermined distance A is about 0.25 inches or less.

19. The apparatus of claim 14, wherein at least one of the sensors is a fiber optic sensor.

20. The apparatus of claim 19, wherein the fiber optic sensor further comprises:
   a computer interface card; and
   a fiber optic receiver electrically connected to the input of the computer interface card for counting the time in which the object is in contact with the striking surface.

21. The apparatus of claim 1, wherein the propelling device fires the object in a horizontal direction.

22. An apparatus for the simultaneous measurement of contact time and Coefficient of Restitution of golf ball, the apparatus comprising:
   a striking surface;
   a propelling device facing the striking surface that fires the golf ball toward the striking surface;
   at least one sensing device at a first position in between the propelling device and the striking surface having a first sensing plane;
   a timing device triggered by the at least one sensing device;
   at least one camera triggered by the at least one sensing device to acquire at least a first and second pair of images before and after the golf ball contacts the striking surface, respectively; and
   a computing unit that calculates Coefficient of Restitution of the object and the contact time between the golf ball and the striking surface.

23. The apparatus of claim 22, wherein each pair of images comprise a first and second image taken at two discrete time intervals.

24. The apparatus of claim 22, further comprising a second sensing device at a second position having a second sensing plane, wherein the second sensing device is parallel and at a predetermined distance A from the striking surface.

25. The apparatus of claim 24, wherein the second sensing device comprises at least one fiber optic sensor.

26. The apparatus of claim 25, wherein the at least one fiber optic sensor comprises a computer interface card and a fiber optic receiver electrically connected to the input of the computer interface card for counting the time in which the object stays past the second sensing device.

27. The apparatus of claim 22, further comprising a second camera to acquire at least a third and fourth pair of images before and after the object contacts the striking surface, respectively.

28. A method of measuring Coefficient of Restitution and contact time of a golf ball comprising the steps of:

provide a propelling device, a striking surface, and a sensing unit located between the striking surface and the propelling device;

firing the golf ball towards the striking surface with the propelling device;

measuring a first velocity of the golf ball before it contacts the striking surface;

measuring impact duration of the golf ball with the striking surface;

measuring a second velocity of the golf ball after it rebounds from the striking surface; and calculating the Coefficient of Restitution.

29. The method of claim 28, further comprising the step of:

providing at least one sensing unit having a measuring field covering at least a portion of space between an initial position of the object and the striking surface, wherein the at least one sensing unit measures the time required for the object to travel a distance in the measuring field of the sensing unit.

30. The method of claim 29, further comprising the step of:

providing a computing unit in communication with the at least one sensing unit that calculates the Coefficient of Restitution of the object and impact duration between the object and the striking surface.

31. The method of claim 30, wherein the mass of the striking surface is at least about 50 times greater than the mass of the object.

32. The method of claim 28, wherein the step of releasing the object is done horizontally.

33. The method of claim 28, wherein the step of releasing the object is done vertically.

34. The method of claim 28, further comprising the step of:

providing at least one camera to acquire at least a first and second pair of images before and after the object contacts the striking surface, respectively.

35. The method of claim 29, further comprising the step of:

providing a second sensing unit having a second measuring field covering a space between the at least one sensing unit and the striking surface, wherein the second sensing unit is parallel and at a predetermined distance from the striking surface.

36. The method of claim 34, further comprising the step of:

providing a second camera to acquire at least a third and fourth pair of images before and after the object contacts the striking surface, respectively.

* * * * *